US009398885B2

(12) United States Patent
Suzuki et al.

(10) Patent No.: US 9,398,885 B2
(45) Date of Patent: Jul. 26, 2016

(54) MOBILE X-RAY DIAGNOSTIC APPARATUS AND METHOD FOR CONTROLLING MOBILE X-RAY DIAGNOSTIC APPARATUS

(71) Applicants: Koichiro Suzuki, Tokyo (JP); Takahiro Yurugi, Tokyo (JP); Yasuo Matsuoka, Tokyo (JP)

(72) Inventors: Koichiro Suzuki, Tokyo (JP); Takahiro Yurugi, Tokyo (JP); Yasuo Matsuoka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 92 days.

(21) Appl. No.: 14/347,763

(22) PCT Filed: Sep. 24, 2012

(86) PCT No.: PCT/JP2012/074395
§ 371 (c)(1),
(2) Date: Mar. 27, 2014

(87) PCT Pub. No.: WO2013/047438
PCT Pub. Date: Apr. 4, 2013

(65) Prior Publication Data
US 2014/0233702 A1 Aug. 21, 2014

(30) Foreign Application Priority Data
Sep. 28, 2011 (JP) ................... 2011-213100

(51) Int. Cl.
*A61B 6/00* (2006.01)
(52) U.S. Cl.
CPC ............ *A61B 6/4405* (2013.01); *A61B 6/42* (2013.01); *A61B 6/4233* (2013.01); *A61B 6/4441* (2013.01); *A61B 6/4452* (2013.01); *A61B 6/4482* (2013.01); *A61B 6/462* (2013.01); *A61B 6/547* (2013.01); *A61B 6/464* (2013.01)

(58) Field of Classification Search
CPC .. A61B 6/4441; A61B 6/4405; A61B 6/4452; A61B 6/4476; A61B 6/587; A61B 6/4429
See application file for complete search history.

(56) References Cited

U.S. PATENT DOCUMENTS

| 6,222,906 B1 | 4/2001 | Sakaguchi et al. |
| 2009/0010394 A1 | 1/2009 | Watanabe |
| 2013/0287171 A1* | 10/2013 | Hibino ................. A61B 6/4405 378/62 |

FOREIGN PATENT DOCUMENTS

| CN | 101339359 A | 1/2009 |
| JP | 60-124903 | 8/1985 |
| JP | 9-173325 A | 7/1997 |
| JP | 11-226001 A | 8/1999 |
| JP | 2000-217808 A | 8/2000 |

(Continued)

OTHER PUBLICATIONS

International Search Report issued in corresponding application No. PCT/JP2012/074395 on Nov. 13, 2012.

(Continued)

*Primary Examiner* — Hoon Song
(74) *Attorney, Agent, or Firm* — Brundidge & Stanger, P.C.

(57) ABSTRACT

The problem addressed by the invention is to always keep an imaging angle of an X-ray detector to an object constant before and after an imaging unit is moved. In order to solve the problem, a mobile X-ray diagnostic apparatus related to the present invention detects a rotation amount of a main body in a horizontal surface due to movement on a floor surface and controls rotation drive of the X-ray detector based on a detection result.

8 Claims, 7 Drawing Sheets

(56) References Cited

FOREIGN PATENT DOCUMENTS

| JP | 2008-000430 A | 1/2008 |
| JP | 2009-011466 A | 1/2009 |

OTHER PUBLICATIONS

International Publication issued in corresponding application No. PCT/JP2012/074395 on Apr. 4, 2013.

* cited by examiner

(12) United States Patent

MOBILE X-RAY DIAGNOSTIC APPARATUS AND METHOD FOR CONTROLLING MOBILE X-RAY DIAGNOSTIC APPARATUS

TECHNICAL FIELD

The present invention relates to a mobile X-ray diagnostic apparatus, in particular, to controlling a position of an X-ray detector.

BACKGROUND ART

There is a surgical mobile C-arm unit including an imaging unit that contains an X-ray source and an X-ray detector as well as two units of monitors to display images sent from the X-ray detector.

The surgical mobile C-arm unit includes a circular X-ray detector using I.I. (Image Intensifier) and a square X-ray detector using FPD (Flat Panel Detector). An image direction toward an object rotates by rotating both the detectors with an imaging unit parallel to the horizontal surface.

As a method to keep an image orientation constant, PATENT LITERATURE 1 discloses a method to keep a detector itself in a certain direction by balancing out rotation amounts of the C-arm and the detector.

CITATION LIST

Patent Literature

PTL 1: Japanese Unexamined Patent Application Publication No. H11-226001

SUMMARY OF INVENTION

Technical Problem

In PTL 1, a rotation amount of an overhead travelling C-arm is detected on the basis of a position of a suspension fixed on a ceiling. Therefore, the suspension fixed on a ceiling can be the basis of rotation amount detection of the C-arm. In case of a surgical mobile C-arm unit, however, there has been a problem in which the PTL 1 method cannot be applied because the basis of a rotation amount cannot be obtained with the imaging unit moving toward a floor surface.

The present invention was made for the above problem and is aimed to provide a mobile X-ray diagnostic apparatus that can keep an image orientation constant regardless of axle support structures before and after the mobile X-ray diagnostic apparatus moves.

Solution to Problem

To solve the above problem, the mobile X-ray diagnostic apparatus related to the present invention is characterized by in that a rotation amount in a horizontal surface of the main body due to the movement on a floor surface is detected and rotary drive of the X-ray detector is controlled based on the detection result.

Advantageous Effects of Invention

According to the present invention, the mobile X-ray diagnostic apparatus that can keep an image orientation constant regardless of axle support structures before and after the mobile X-ray diagnostic apparatus moves and the controlling method can be provided.

DESCRIPTION OF EMBODIMENTS

Hereinafter, embodiments to which the present invention is applied will be described.

A mobile X-ray diagnostic apparatus of the present invention is a mobile X-ray diagnostic apparatus including an X-ray source to irradiate an X-ray; an X-ray detector to detect an X-ray transmitted through an object; a holding unit to hold the X-ray source and X-ray detector facing each other; an X-ray detector rotation driving unit to drive rotationally the X-ray detector to the holding unit; and a main body to support the holding unit movably on a floor surface. The mobile X-ray diagnostic apparatus is characterized in that the first detection unit to detect a rotation amount on a horizontal surface of the main body by movement on the floor surface and an X-ray detector control unit to control rotary drive of the X-ray detector using the X-ray detector rotation driving unit based on a detection result in the first detection unit are included.

In addition, the X-ray detector control section is characterized in that a target rotation amount calculation unit that calculates a target rotation amount required to change an orientation of the X-ray detector that moves with the main body to the original orientation of the main body based on the rotation amount detected by the first detection unit and an X-ray detector rotation control unit that commands the X-ray detector rotation driving unit to rotate the X-ray detector based on the target rotation amount calculated by the target rotation amount calculation unit are included.

In addition, further equipped with a supporting unit to support the holding unit with respect to the main body rotatably and the second detection unit to detect a rotation amount of the supporting unit, the target rotation amount calculation unit is characterized in that a target rotation amount based on a rotation amount detected by the first detection and a rotation amount detected by the second detection unit are calculated.

In addition, further equipped with a command entry unit to enter commands for start and end of detection by the first detection unit and the second detection unit, the first detection unit and the second detection unit are characterized in that a displacement from a time point where a detection start command by the command entry unit was entered to a time point where a detection end command is entered as a rotation amount is detected based on the positions of the main body and the supporting unit.

In addition, equipped with the third detection unit to detect a rotation amount of the X-ray detector, the target rotation amount calculation unit calculates the target rotation amount in further addition to a rotation amount of the X-ray detector detected by the third detection unit while the first detection unit and the second detection unit start and end the detection. The third detection unit detects a rotation amount of the X-ray detector rotated by a command for rotation by the target rotation amount from the X-ray detector rotation control unit to the X-ray detector rotation drive unit. The X-ray detector rotation control unit determines whether a rotation equivalent to the target rotation amount has ended or not based on the angle deviation between the relevant rotation amount and the target rotation amount.

In addition, the main body is further equipped with wheels to move on the floor surface, and the first detection unit is characterized in that it is composed of a sensor to detect a rotation amount of the wheels.

In addition, the first detection unit is characterized in that it is composed of a sensor to detect angular acceleration of the main body.

In addition, the second detection unit is characterized in that it is composed of a sensor to detect a rotation amount of the supporting unit or a sensor to detect angular acceleration of the supporting unit.

In addition, the third detection unit is characterized in that it is composed of a sensor to detect a rotation amount of the X-ray detector rotation driving unit or a sensor to detect angular acceleration of the X-ray detector.

In addition, further equipped with a radiation button that enters a fluoroscopy command to detect a dynamic picture image by irradiating an X-ray from the X-ray source, the command entry unit is composed using the radiation button, starts the detection when a command to start fluoroscopy is entered from the radiation button. The first detection unit and the second detection unit is characterized in that the detection is continued until a command to end fluoroscopy is entered from the radiation button.

In addition, a control method of a mobile X-ray diagnostic apparatus of the present invention is a control method of a mobile X-ray diagnostic apparatus equipped with the main body to support the X-ray detector that detects a transmitting X-ray irradiated from the X-ray source to an object movably on a floor surface and is characterized in that a step to detect a rotation amount of the main body on a horizontal surface by the movement on the floor surface and a step to rotationally drive the X-ray detector based on the detection result are included.

Hereinafter, embodiments of the present invention will be described in detail with reference to the diagrams. Components having the same functions and procedures of the same processing content are denoted by the same reference numerals, and explanation thereof will be omitted.

Figure 1:
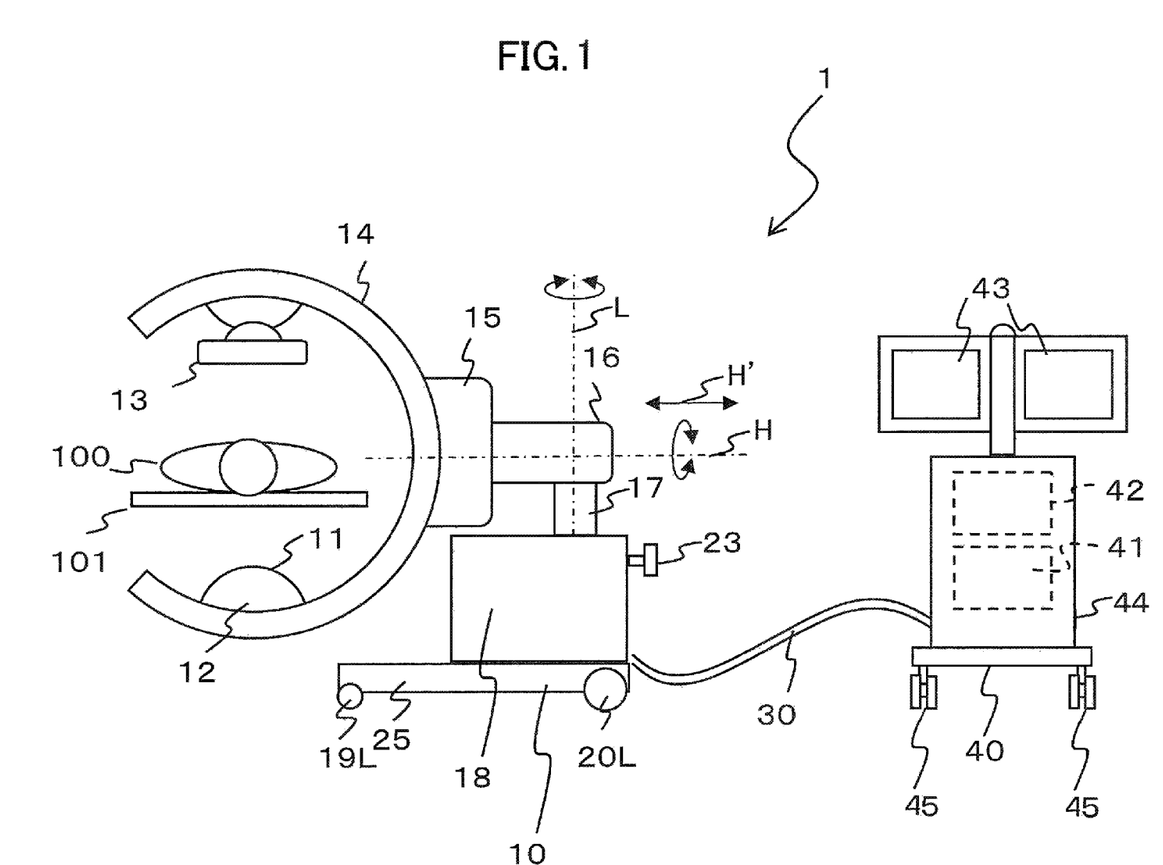
FIG. 1 is an entire framework showing the outline framework of the mobile X-ray diagnostic apparatus related to the present embodiment.

A mobile X-ray diagnostic apparatus related to the present invention is a mobile X-ray diagnostic apparatus that is composed so that it is freely movable on a floor surface and enables to fluoroscope (X-ray imaging by a dynamic picture image) and image (X-ray imaging of still images) by placing closely to an object. First, the schematic configuration of a mobile X-ray diagnostic apparatus related to the present embodiment will be described with reference to FIG. 1. FIG. 1 is a block diagram showing the configuration of the mobile X-ray diagnostic apparatus related to the present embodiment.

The mobile X-ray diagnostic apparatus 1 is equipped with mainly two types of units i.e., the imaging unit 10 that is a unit to perform fluoroscopic imaging and the monitoring unit 40 that is a unit to display a fluoroscopic image as shown in FIG. 1. The imaging unit 10 and the monitoring unit 40 are connected electrically with the cable 30.

The imaging unit 10 includes: the X-ray source 11 to irradiate an X-ray to an object 100 placed on the bed 101; a limiting device that sets a X-ray irradiation region for the object 100 (omitted to be shown in the figure); the high voltage generator 12 that provides electricity for the X-ray source; the X-ray detector 13 that detects an X-ray transmitted through an object 100 and that is installed at a position facing the X-ray source across the object 100; the C-arm 14 equipped with a C-shape arm to support the X-ray source 11 and the X-ray detector 13 with them facing each other; the main body 18 equipped with a control portion to control each component of the imaging unit 10 and communicate with the monitoring unit 40; and the carriage 25 that carries the main body 18 and moves on a floor surface.

The body unit 18 is equipped with the vertical pillar 17 that is installed in a vertical direction to a floor surface; the rotation support portion 16 that is supported by the vertical pillar 17 and protruding toward the direction horizontal to a floor surface and the installing direction of the C-arm 14; and the supporting unit 15 that is installed successively on the C-arm installation direction side of the rotation support portion 16 on its upper portion. The vertical pillar 17 supports the rotation support portion 16 toward the direction vertical to a floor surface movably and further rotatably with the axis L (hereinafter referred to as a vertical axis) extended along a vertical direction centered.

The rotation support portion 16 movably supports the supporting unit 15 parallel to a floor surface i.e. along the arrow H' direction (movably supports in a lateral direction) as well as rotatably with the axis H (hereinafter referred to as a horizontal axis) horizontal to a floor surface centered. The supporting unit 15 supports the C-arm 14 along the arc direction rotatably. Additionally, the carriage 25 includes the wheels 20 (the left wheel 20L is drawn in FIG. 1) to move the carriage 25 manually and the flexible casters 19 (the left caster 19L is drawn in FIG. 1) driven by the wheels 20 (20L). To assist operators, it may be better to provide the wheels 20 with a motor so that the wheels 20 rotate by the motor to drive the flexible casters 19.

The handle 23 is installed on the side surface opposite to the side where the C-arm 14 of the body unit 18 to hold when an operator moves the imaging unit 10. It may be better to provide the handle 23 with a braking mechanism that locks the wheels 20 to prevent unintentional movement due to an external force after placing the imaging unit 10 in place. The braking mechanism can be composed so that it is connected to the handle 23 to enable to lock or release the brake while an operator is holding the handle 23. Hence, the imaging unit 10 can move by itself and can be placed at an arbitrary position for the object 100.

The monitoring unit 40 includes: the X-ray detector control section 41 that controls the X-ray detector 13 and the X-ray source 11; the image processing device 42 that processes images detected by the X-ray detector 13; the monitor 43 that displays the processed images; the main body 44 that includes the X-ray detector control section 41, the image processing device 42, and the monitor 43 to display processed images and that can move freely on a horizontal surface; and the flexible casters 45 that carry the main body 44 and that move and move rotationally in a horizontal surface.

First Embodiment

Figure 2:
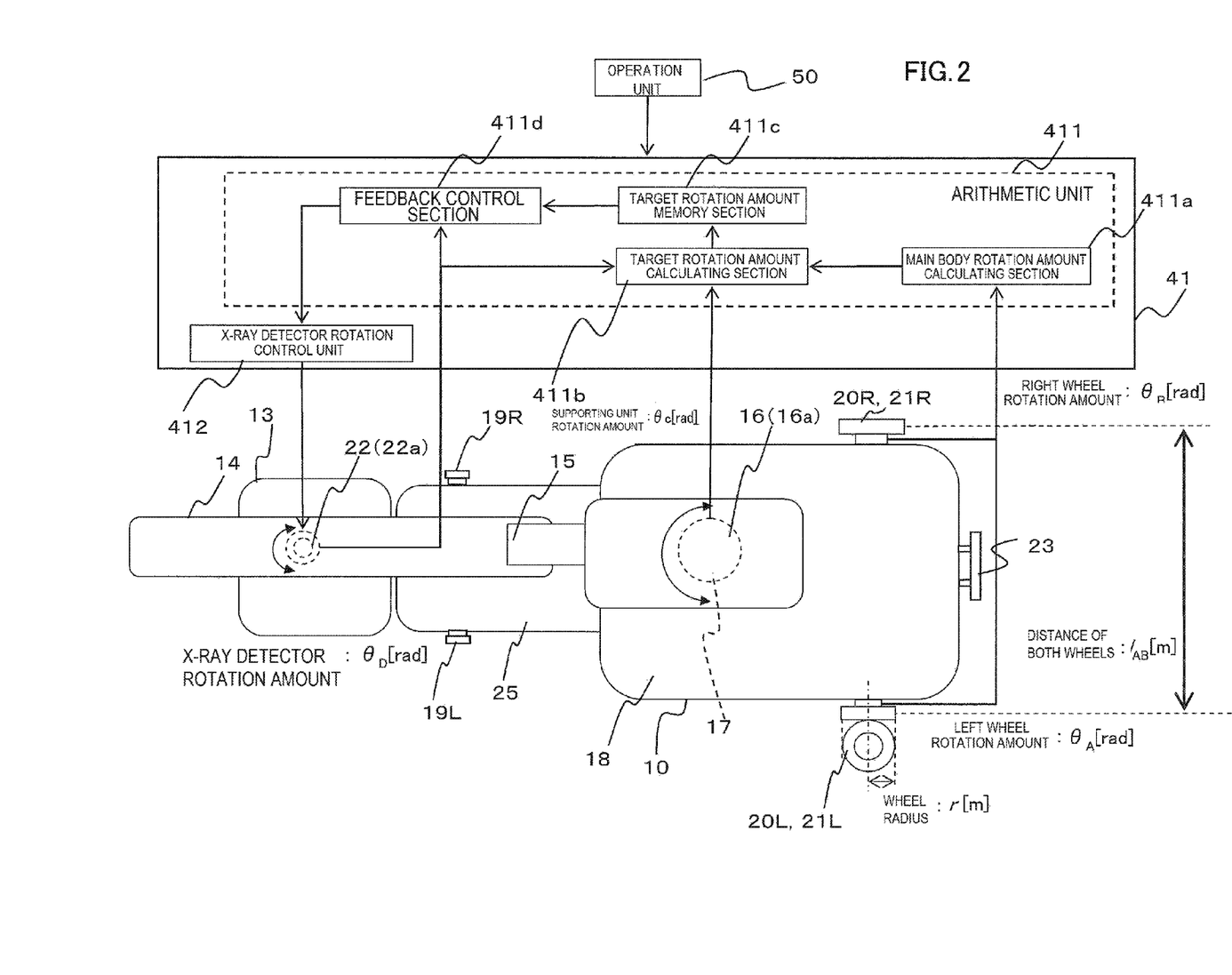
FIG. 2 is an explanatory diagram showing the component of the imaging unit 10 related to the first embodiment.
Figure 3:
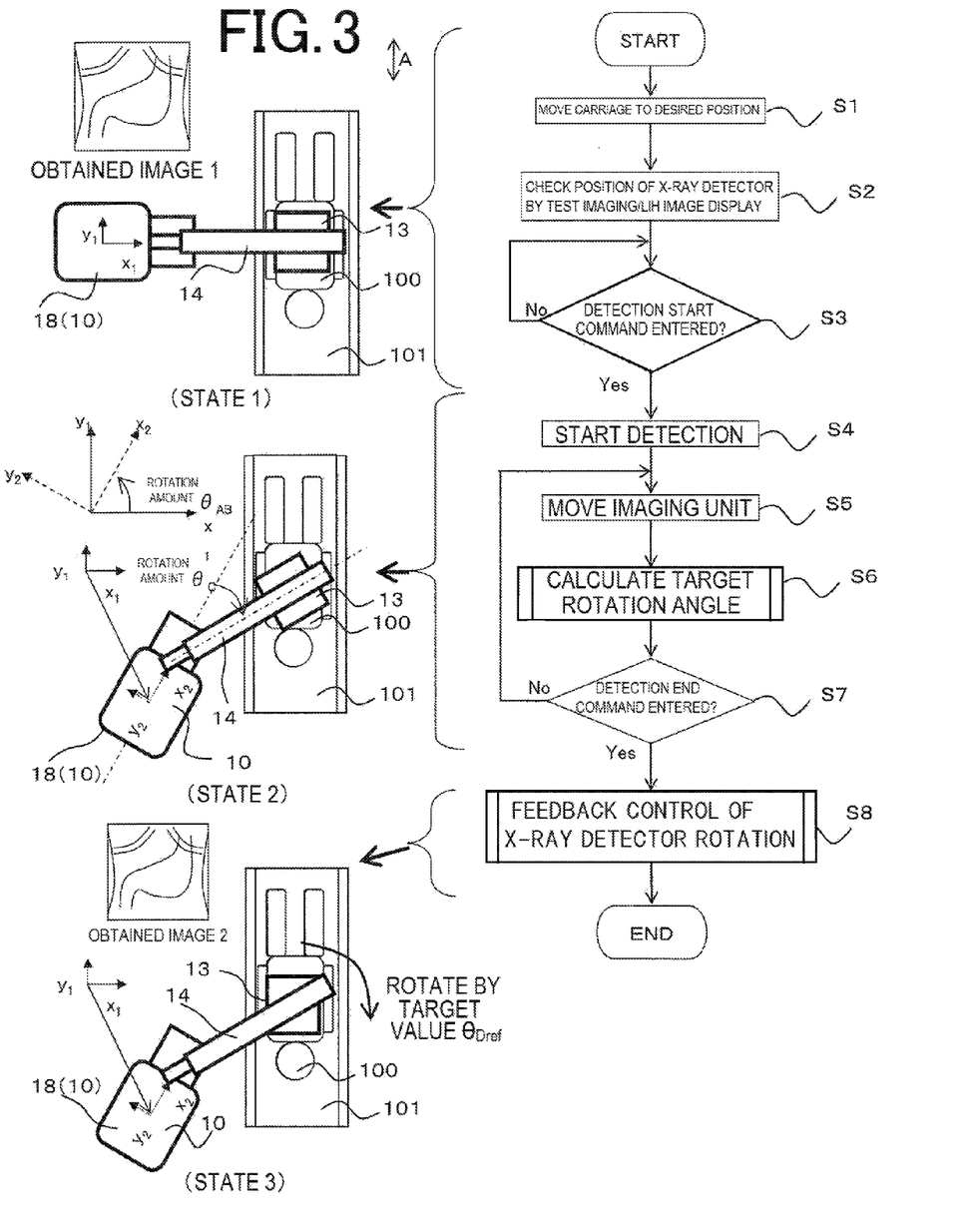
FIG. 3 is an explanatory diagram showing the processing procedure for the mobile X-ray diagnostic apparatus.
Figure 4:
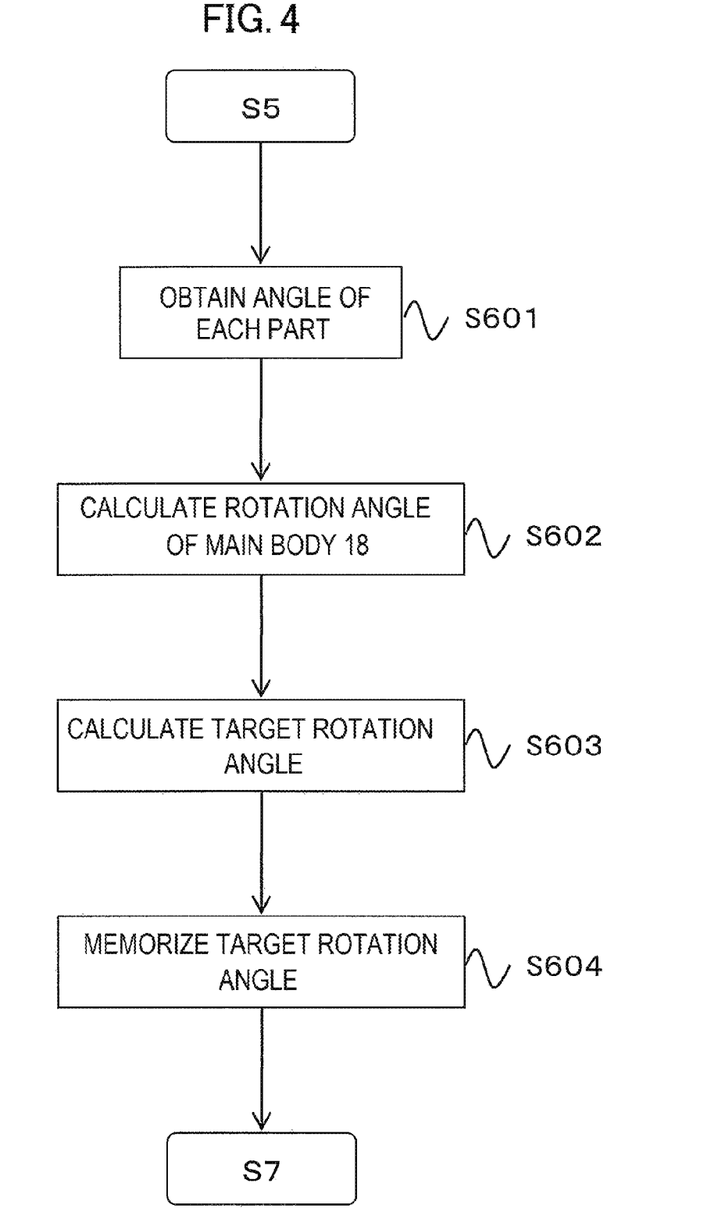
FIG. 4 is a flow chart showing the processing procedure for target rotary angle calculation process.
Figure 5:
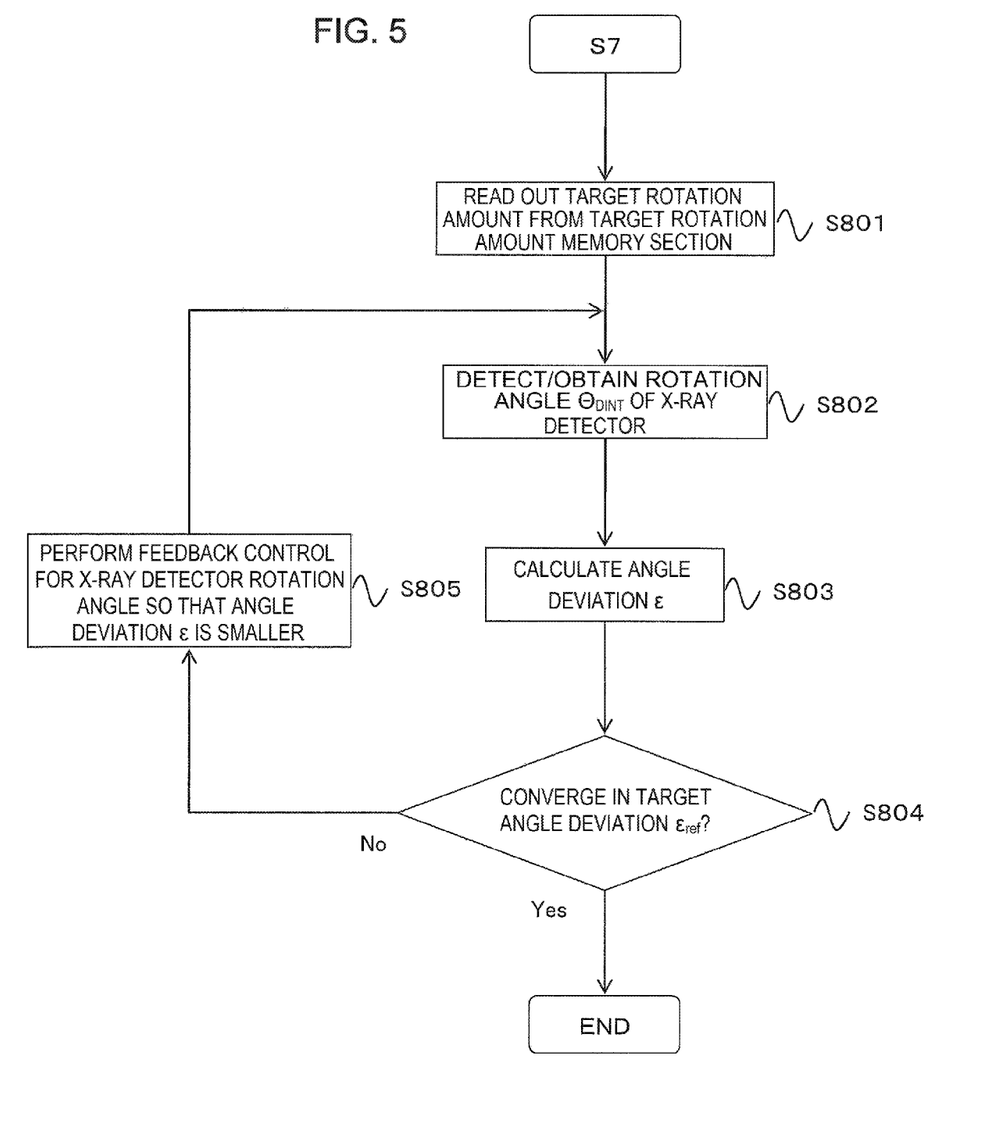
FIG. 5 is a flow chart showing the processing procedure for feedback process for an X-ray detector angle.

Next, the first embodiment will be described based on FIGS. 2 to 5. FIG. 2 is an explanatory diagram showing the configuration of the imaging unit 10 related to the first embodiment. FIG. 3 is an explanatory diagram showing a processing procedure for a mobile X-ray diagnostic apparatus. FIG. 4 is a flow chart showing a processing procedure for a target rotation angle calculation process. FIG. 5 is a flow chart showing a processing procedure for a feedback process of an X-ray detector rotation angle.

As shown in FIG. 2, the X-ray detector 13 is installed rotatably in a horizontal surface to the C-arm 14 via the X-ray detector rotation driving unit 22. Although omitted to be shown in the figure, the X-ray detector rotation driving unit 22 is equipped with the X-ray detector rotation amount sensor 22a that detects a rotation amount of the X-ray detector 13. A rotary encoder that detects the number of rotation and a rotation amount of the X-ray detector rotation driving unit 22 can be used for the X-ray detector rotation amount sensor 22a. The X-ray detector rotation amount sensor 22a detects an X-ray detector rotation amount $\theta_D$ [rad] that is a rotation amount of the X-ray detector 13. It may be better to rotate the X-ray detector 13 manually in addition to rotating by the X-ray detector rotation driving unit 22. In this case, the X-ray detector rotation amount sensor 22a detects a manual rotation amount also.

The rotation support portion 16 has a mechanism that rotates the supporting unit 15 manually or automatically in a vertical surface and horizontal surface and the supporting unit rotation amount sensor 16a that detects a rotation amount of the supporting unit 15 though omitted to be shown in the figure. A rotary encoder that detects the number of rotation and a rotation amount of the rotation support portion 16 can be used for the supporting unit rotation amount sensor 16a. The supporting unit rotation amount sensor 16a detects a supporting unit rotation amount $\theta_C$ [rad] that is a rotation amount of the supporting unit 15 for the rotation support portion 16.

The wheels 20 consist of the right wheel 20R and left wheel 20L. The right wheel rotation amount sensor 21R to detect a rotation amount of the right wheel 20R is installed near the right wheel 20R of the main body 18. The left wheel rotation amount sensor 21L to detect a rotation amount of the left wheel 20L is installed near the left wheel 20L of the main body 18. For example, a rotary encoder which detects a movement amount (rotation amount) and the number of rotation of wheels can be used for the right wheel rotation amount sensor 21R and left wheel rotation amount sensor 21L. The right wheel rotation amount sensor 21R and left wheel rotation amount sensor 21L. A right wheel rotation amount 20L $\theta_B$ [rad] and a left wheel rotation amount 20L $\theta_A$ [rad] are detected respectively for each rotation amounts of the right wheel 20R and left wheel 20L. The flexible casters 19 include the right caster 19R and left caster 19L.

The X-ray detector control section 41 includes the arithmetic unit 411 and the X-ray detector rotation control unit 412. The X-ray detector rotation control unit 412 outputs a rotation command signal of the X-ray detector 13 to the previous X-ray detector rotation driving unit 22 and controls rotation actions of the X-ray detector 13 by the X-ray detector rotation driving unit 22.

The arithmetic unit 411 includes: the main body rotation amount calculating section 411a (Hereinafter "main body rotation amount" is described as $\theta_{AB}$) that obtains a left wheel rotation amount 20L $\theta_A$ [rad] and a right wheel rotation amount 20L $\theta_B$ [rad] detected by the left wheel rotation amount sensor 21L and right wheel rotation amount sensor 21R to convert these rotation amounts into a rotation amount in a horizontal surface of the main body 18; the target rotation amount calculating section 411b (Hereinafter "target rotation amount" is described as $\theta_{ref}$) that obtains an X-ray detector rotation amount $\theta_D$ [rad] from the X-ray detector rotation amount sensor 22a, a supporting unit rotation amount $\theta_C$ [rad] from the supporting unit rotation amount sensor 16a, and additionally a main body rotation amount $\theta_{AB}$ calculated above to calculate a target rotation amount required to balance out rotation in a horizontal surface of the X-ray detector 13 due to movement of the imaging unit 10 based on rotation amounts of these respective parts; the target rotation amount memory section 411c that memorizes a target rotation amount $\theta_{ref}$; and the feedback control section 411d that continues to calculate a rotation amount of the X-ray detector 13 required to reach the target rotation amount $\theta_{ref}$.

If the main body rotation amount calculating section 411a requires a parameter to convert rotation amounts of a left wheel rotation amount 20L $\theta_A$[rad] and a right wheel rotation amount 20L $\theta_B$[rad] into a rotation amount in a horizontal surface of the main body 18, for example, a distance value $I_{AB}$[m] between the left wheel 20L and the right wheel 20R as well as a radius value r[m] of the left wheel 20L and the right wheel 20R may be memorized in the main body rotation amount calculating section 411a in advance.

The feedback control section 411d outputs a signal that shows a required rotation amount to the X-ray detector rotation control unit 412. The X-ray detector rotation control unit 412 outputs a rotation command signal including rotation amount information to the X-ray detector rotation driving unit 22 to rotate the X-ray detector 13. The X-ray detector rotation amount sensor 22a always detects a rotation amount of the X-ray detector 13 and outputs the rotation amount to the feedback control section 411d. The feedback control section 411d calculates a rotation amount again based on a detected signal of the X-ray detector rotation amount sensor 22a and a target rotation amount.

The X-ray detector control section 41 is installed in the imaging unit 10 or the monitoring unit 40 and electrically connected to the operation unit 50 that receives an input signal by operator's operation. The operation unit 50 includes a control command input button to enter a command to start and end X-ray detector rotation control and an X-ray radiation button to enter a command to start and end fluoroscopy by the mobile X-ray diagnostic apparatus 1.

Pressing a control command input button performs a starting action of X-ray detector rotation control, and pressing the control command input button again performs an ending action of the rotation control. Additionally, pressing the X-ray radiation button to start fluoroscopy performs a starting action of X-ray detector rotation control, and releasing the X-ray radiation button displays a Last Image Hold (LIH) image on the monitor 43. At the same time, the ending action of the rotation control may be performed. Additionally, a braking mechanism of the imaging unit 10 works, and the starting action of the rotation control may be performed with applying a brake to the imaging unit 10 as a trigger. Additionally, detection and calculation may be performed until the main power supply is OFF after the detection and calculation start at the same time when the main power supply is ON.

Next, a processing procedure for a rotation control process by the X-ray detector 13 of a mobile X-ray diagnostic apparatus related to the first embodiment will be described with reference to FIGS. 3 to 5. Hereinafter, explanation will be given along the respective steps in the flow chart in FIG. 3.

(Step S1)

First, the carriage 25 is moved to a desired position. That is, the mobile X-ray diagnostic apparatus 1 related to the present embodiment is moved closer to an object, and the X-ray source 11 and the X-ray detector 13 are schematically positioned at a procedure target site by movement of the imaging unit 10 and drive of the C-arm 14 (S1).

(Step S2)

An operator presses the X-ray radiation button on the operation unit 50 and tentatively performs X-ray fluoroscopy, and an X-ray image of the final frame is displayed as an LIH image on the monitor 43. The operator visually checks the LIH image to check a position of the X-ray detector 13 (S2). A sample of the LIH image is shown in the obtained image 1. In the obtained image 1, the vertical direction of the image corresponds with the head-foot direction of the object 100, and the procedure target site is almost centered in the obtained image 1. If the position of the X-ray detector 13 is allowable for an operator, the operator performs the next procedure such as fluoroscopy and imaging at the same position.

The state 1 shows a positional relationship among the imaging unit 10, the object 100, and the bed 101 in Step S2. The head-foot direction of the object 100 (the arrow A direction) corresponds with a longitudinal direction of the bed 101. When defining an x1 axis parallel to a long side and a y1 axis parallel to a short side and assuming a rectangular coordinate system of an x1-y1 axis in the main body 18 having a rectangular-shaped surface, the C-arm 14 is supported parallel to the x1 axis for the main body 18. Additionally, the rectangular-shaped X-ray detector 13 is positioned so that the short side is parallel to the head-foot direction and the long side is vertical to the head-foot direction.

(Step S3)

The imaging unit 10 enters a waiting state for a detection start command. That is, an operator performs an operation to generate a trigger for rotation amount detection start and proceeds to Step S4 when a position of the imaging unit 10 needs to be moved due to a position change between an operator and practitioner after performing the procedure.

On the other hand, if the imaging unit 10 does not need to be moved, it remains in the waiting state in Step S3 (S3). In the present embodiment, turning ON a control command input button on the operation unit 50 generates a trigger. However, the trigger may be generated by not only an input operation of a trigger signal from an operator but also displaying an LIH image for example. In this case, the present step is omitted, and the trigger is generated by the LIH image display in the previous Step S2.

(Step S4)

When the trigger is generated, the X-ray detector control section 41 performs a rotation control start action (S4).

Specifically, first, respective sensors i.e., the X-ray detector rotation amount sensor 22a, the supporting unit rotation amount sensor 16a, the right wheel rotation amount sensor 21R, and the left wheel rotation amount sensor 21L set respective positions of the supporting unit 15, the X-ray detector 13, the right wheel 20R, and the left wheel 20L as benchmark positions. Afterward, displacement amounts from the benchmark positions are calculated as rotation amounts. Therefore, for example, if a rotation control end command to be described below is entered after the supporting unit 15 rotates 90 degrees clockwise and then rotates 45 degrees counterclockwise from the benchmark position, the detection value of the supporting unit rotation amount $\theta_C$ is detected as 45 degrees clockwise. An X-ray detector rotation amount $\theta_D$, left wheel rotation amount $\theta_A$, and right wheel rotation amount $\theta_B$ are also detected similarly.

(Step S5)

An operator moves the imaging unit 10 along with the X-ray detector 13 (S5).

The state 2 shows a positional relationship among the imaging unit 10, the object 100, and the bed 101 in Step S5. The head-foot direction of the object 100 corresponds with a longitudinal direction of the bed 101 and is not changed from the state 1. When defining an x2 axis parallel to a long side of the moved main body 18 and a y2 axis parallel to a short side and assuming a rectangular coordinate system of an x2-y2 axis, the C-arm 14 rotates an angle $\theta_C$ from the x2 axis of the main body 18. Also, a rectangular coordinate system of the x2-y2 axis rotates an angle $\theta_{AB}$ from a rectangular coordinate system of the x1-y1 axis.

(Step S6)

Calculation process of a target rotation angle is performed (S6). The processing procedure for the present step will be explained along the respective steps in FIG. 4.

In Step S601, respective rotary encoders i.e., the X-ray detector rotation amount sensor 22a, the supporting unit rotation amount sensor 16a, the left wheel rotation amount sensor 21L, and the right wheel rotation amount sensor 21R detect $\theta_D$ [rad], $\theta_C$ [rad], $\theta_A$ [rad], and $\theta_B$ [rad]. $\theta_C$ [rad] and $\theta_D$ [rad] show a rotation angle $\theta_C$ of the supporting unit 15 and a rotation angle $\theta_D$ of the X-ray detector rotation driving unit 22 respectively and are output to the target rotation amount calculating section 411b. On the other hand, values $\theta_A$ and $\theta_B$ of the rotary encoders are output to the main body rotation amount calculating section 411a. Also, "Movement of an imaging unit" mentioned in the present step includes a case where a movement amount is 0, that is, the imaging unit is not actually moved. In this case, respective output sensor values are 0.

In Step S602, the main body rotation amount calculating section 411a is converted into a rotation amount $\theta_{AB}$ of the main body 18 of the imaging unit 10 using the following formula (1) (S602).

$$\theta_{AB} = \frac{r}{l_{AB}}(\theta_B - \theta_A) \quad (1)$$

$\theta_{AB}$ [rad]: Carriage rotation amount, r [m]: Wheel radius, $l_{AB}$ [m]: Distance between both wheels, θB [rad]: Right wheel rotation amount, $\theta_A$ [rad]: Left wheel rotation amount The calculated rotation amount $\theta_{AB}$ of the main body 18 of the imaging unit 10 is output to the target rotation amount calculating section 411b.

In Step S603, the target rotation amount calculating section 411b performs calculation of a rotation angle (target angle: $\theta_{ref}$) required to balance out rotation movement of the X-ray detector 13 due to movement of the imaging unit 10 (S603). The target rotation amount calculating section 411b calculates a target rotation angle $\theta_{Dref}$ of the X-ray detector rotation driving unit 22 using the following formula (2).

$$\theta_{Dref} = \theta_{AB} + \theta_C + \theta_D \quad (2)$$

$\theta_{Dref}$ [rad]: a target rotation angle of the X-ray detector rotation driving unit, $\theta_{AB}$ [rad]: a rotation angle of the main body 18

$\theta_C$ [rad]: a rotation angle of the supporting unit 15, $\theta_D$ [rad]: a rotation angle of the X-ray detector rotation unit Also, after Step 4, for example, in a case where an operator rotates the X-ray detector 13 manually, $\theta_D$ is a value higher than 0 or lower than 0. In a case where the X-ray detector 13 is not rotated, $\theta_D$ is 0.

In Step S604, the target rotation amount memory section 411c memorizes a calculated target rotation angle $\theta_{ref}$ (S604).

(Step S7)

Whether a detection end command is entered or not is judged. If a detection end command is entered, this proceeds to Step S8. If not, this goes back to Step S5 and continues to detect a rotation amount (S7).

(Step S8)

Feedback control of an X-ray detector rotation angle is performed (S8). The processing procedure for the present step will be explained along the respective steps in FIG. 5.

In Step S801, the feedback control section 411d reads out a target rotation angle $\theta_{Dref}$ memorized in the target rotation amount memory section 411c (S801).

In Step S802, the X-ray detector rotation amount sensor 22a detects a rotation angle $\theta_{Dint}$ at a current position for the benchmark position of the X-ray detector 13 and outputs it to the feedback control section 411d (S802).

In Step S803, the feedback control section 411d calculates a difference between a target rotation angle $\theta_{Dref}$ and $\theta_{Dint}$ as an angle deviation ϵ using the formula (3) (S803).

$$\epsilon = \theta_{Dref} - \theta_{Dint} \quad (3)$$

ϵ[rad]: a deviation of a target rotation angle $\theta_{Dref}$ and a current rotation angle $\theta_{Dint}$ $\theta_{Dint}$ [rad]: a rotation angle at a current position for the benchmark position of the X-ray detector 13

In Step S804, the feedback control section 411d reads out a target angle deviation $\epsilon_{ref}$ that is a preliminarily prepared (memorized) constant number for the convergence test and judges whether an angle deviation ϵ satisfies the formula (4) or not (S804).

$$|\epsilon| < \epsilon_{ref} \quad (4)$$

$\epsilon_{ref}$[rad]: a target angle deviation

If an angle deviation ϵ satisfies the formula (4), a series of processes ends. If not, this proceeds to Step S805.

In Step S805, the feedback control section 411d outputs a value of an operation amount for the X-ray detector rotation control unit 412 to the X-ray detector rotation control unit 412 using the formula (5).

$$y = \epsilon \times Kp \quad (5)$$

y: an operation amount for the X-ray detector rotation control unit 412

Kp: a feedback gain

In the X-ray detector rotation control unit 412, an operation amount y is converted into an output amount suitable for rotation drive (such as electric current and voltage), and the X-ray detector rotation driving unit 22 rotates the X-ray detector 13 according to an output amount to perform feedback control (S805).

After going back to Step S802, the processes from Step S802 to Step S805 are repeated until an angle deviation ϵ converges in a target angle deviation $\epsilon_{ref}$.

The state 3 in FIG. 3 shows a positional relationship among the imaging unit 10, the object 100, and the bed 101 when ending feedback control. The head-foot direction of the object 100 corresponds with a longitudinal direction of the bed 101 and is not changed from the states 1 and 2. Additionally, the position of the main body 18 is not changed from the state 2. However, the X-ray detector 13 rotates a target angle $\epsilon_{Dref}$ on the C-arm 14. Consequently, in the obtained image 2, the vertical direction of an image corresponds with the head-foot direction of the object 100 similarly to the obtained image 1. Even if the imaging unit 10 is moved, procedure target sites of an object are imaged in the same direction in the obtained images 1 and 2.

According to the present embodiment, it is possible to keep an operator from being aware of moving the imaging unit 10 because an orientation of a procedure target site in an obtained image is kept constant even before and after the imaging unit 10 is moved. Additionally, if a square X-ray detector (ex. FPD) is installed as the X-ray detector 13, a large field of view that a square X-ray detector originally has can be acquired because the X-ray detector 13 rotates by itself even after moving the imaging unit 10. Moreover, because manual orientation adjustment due to movement of the imaging unit 10 is not required for the X-ray detector 13, skill gaps can be filled among operators. Also, rotation control and feedback control may be set to start at the same time as trigger generation other than the above explanation.

Second Embodiment

Figure 6:
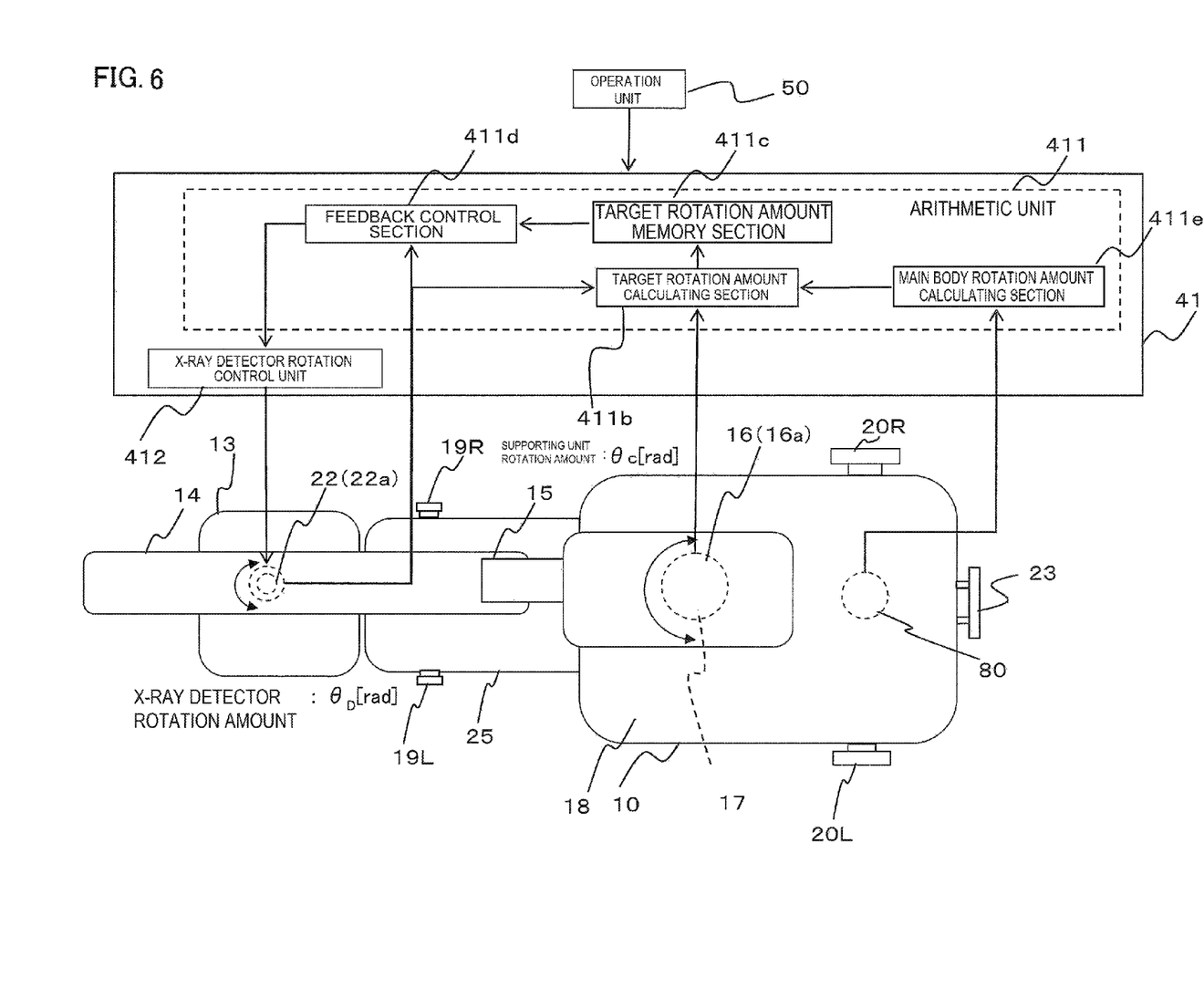
FIG. 6 is an explanatory diagram showing the composition of the imaging unit 10 related to the second embodiment.

The second embodiment will be described with reference to FIG. 6. FIG. 6 is an explanatory diagram showing the configuration of the imaging unit 10 related to the second embodiment.

The imaging unit 10 related to the second embodiment includes not a rotary encoder but the angular acceleration sensor (gyro sensor) 80 and the main body rotation amount calculating section 411e that calculates a rotation amount $\theta_{AB}$ by numerically integrating each angular acceleration $\theta''_{AB}$ detected by the angular acceleration sensor 80 as a sensor to detect a movement amount of the main body 18. Also, a rotation amount $\theta_{AB}$ obtained by numerically integrating each angular acceleration $\theta''_{AB}$ by the main body rotation amount calculating section 411e is output to the target rotation amount calculating section 411b to be used in calculation for a target rotation amount $\theta_{Dref}$ similarly to the first embodiment.

Although sensors are required respectively for left and right wheels one by one to detect an orientational movement amount (rotation amount) of the main body 18 of the imaging unit in the first embodiment, the number of sensors can be reduced because only one angular acceleration sensor is used in the present embodiment. Additionally, even if radiuses of wheels and a distance between both wheels differ, there is no need to change a function to calculate a rotation amount of the imaging unit 10 in a sensor and the X-ray detector control section 41.

<The Other Embodiment>

The previous first and second embodiments show only an example of embodiment, and the present invention is not limited to these embodiments. Various embodiments can be applied without deviating from the scope of the invention. For example, a gyro sensor may be installed in a rotation part where a rotary encoder is installed instead of the rotary encoder. Also, although rotation parts in a mobile X-ray diagnostic apparatus are a total of three parts: the X-ray detector 13, the supporting unit 15, and the main body 18 in the previous embodiments, the number of the rotation parts may be increased or decreased due to a design change such as changing the C-arm 14 to a multi-joint type. In this case, a target rotation amount $\theta_{Dref}$ may be calculated by detecting a rotation amount of all the rotation parts including the increment and decrement.

Figure 7:
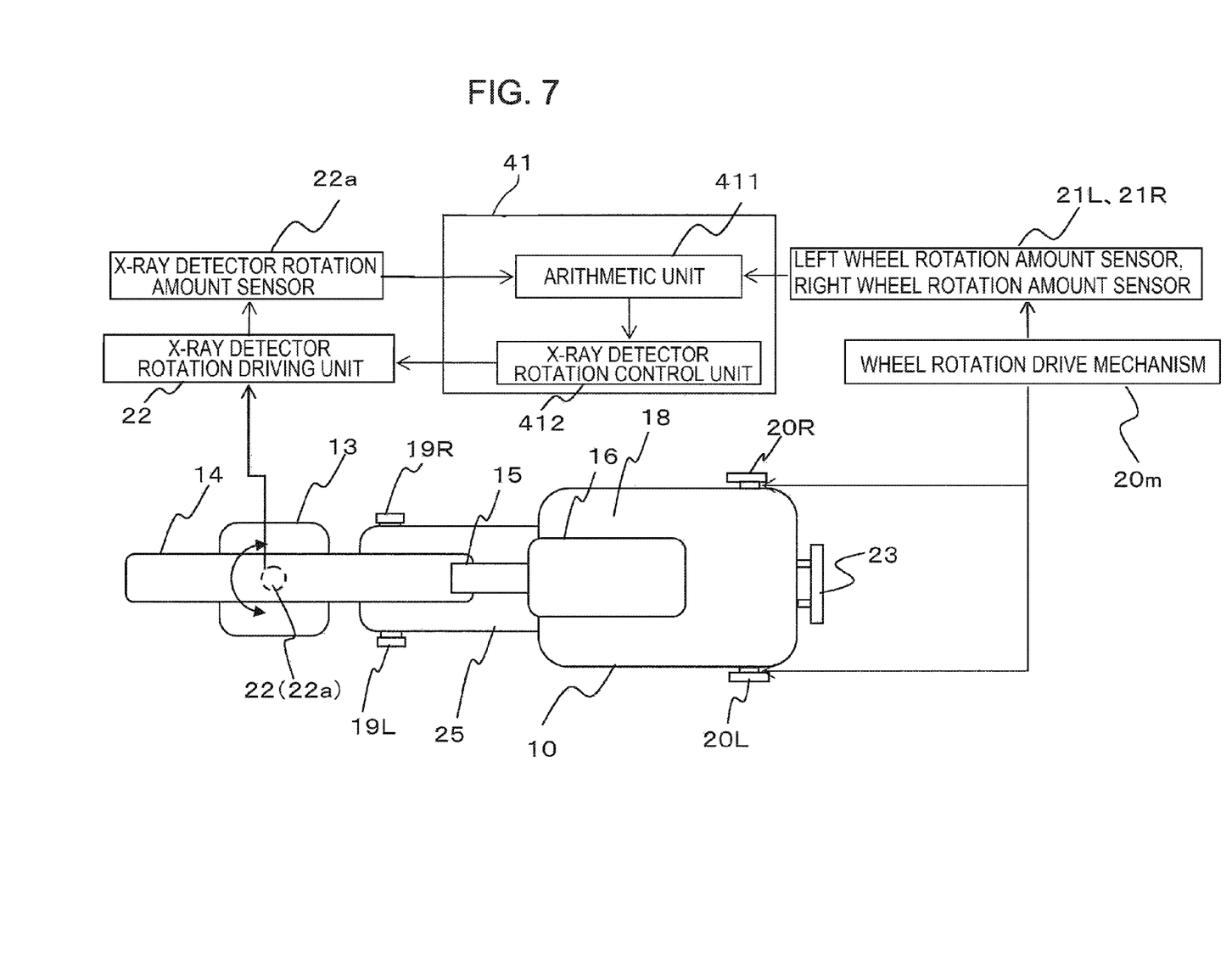
FIG. 7 is an explanatory diagram showing the composition of the imaging unit 10 related to the other embodiments.

Additionally, the other embodiment will be described with reference to FIG. 7. FIG. 7 is an explanatory diagram showing the configuration of the imaging unit 10 related to the other embodiment. As shown in FIG. 7, the present invention can be also applied to the imaging unit 10 where the C-arm 14 is fixed at the main body 18. In this case, the imaging unit 10 includes a sensor to detect a rotation amount of the main body 18 and the X-ray detector rotation amount sensor 22a. Additionally, a mobile X-ray diagnostic apparatus in FIG. 7 includes the wheel rotation drive mechanism 20m that rotationally drives the left wheel 20L and the right wheel 20R. Therefore, the wheel rotation drive mechanism 20m includes the left wheel rotation amount sensor 21L and the right wheel rotation amount sensor 20R, and they detects the number of rotation of the left wheel and the right wheel rotationally driven by the wheel rotation drive mechanism 20m. The arithmetic unit 411 converts the number of rotation into a main body rotation amount and calculates a target rotation amount. Then, feedback control of the X-ray detector rotation control unit 412 is performed using the target rotation amount.

Rotation amount detection of the main body 18 may be performed using an angular acceleration sensor instead of the left wheel rotation amount sensor 21L and the right wheel rotation amount sensor 20R. Also, a rotary encoder and an angular acceleration sensor may be used as the X-ray detector rotation amount sensor 22a.

Also, the X-ray detector control section 41 is installed in the monitoring unit 40 in the first and second embodiments, but it may be also installed in the imaging unit 10. Additionally, the order of the steps in the processing procedure may be changed to an extent where the present invention can be effective without limiting to the flow charts in FIGS. 3, 4, and 5. For example, when calculating a target rotation angle in Step S6, only Step S601 may be performed before Step S7, and Step S602 and the subsequent processes may be performed after Step S7. In this case, output values of the respective sensors continue to be detected to calculate a rotation angle or a target rotation angle of the main body 18 after a detection end command.

REFERENCE SIGNS LIST

1: mobile X-ray diagnostic apparatus
10: imaging unit
11: X-ray source
12: high voltage generator
13: X-ray detector
14: C-arm
15: supporting unit
16: rotation support portion
17: vertical pillar
18: main body
19: flexible casters
20: wheels
30: cable
40: monitoring unit
41: X-ray detector control section
42: image processing device
43: monitor
44: main body
45: flexible casters

The invention claimed is:

1. A mobile X-ray diagnostic apparatus, comprising:
an X-ray source irradiating an X-ray;
an X-ray detector detecting the X-ray transmitted through an object;
a holding unit holding the X-ray source and the X-ray detector facing each other;
an X-ray detector rotation driving unit rotationally driving the X-ray detector for the holding unit;
a movably main body supporting the holding unit on a floor surface;
a first detection unit detecting a rotation amount of the main body in a horizontal surface by a movement on the floor surface;
an X-ray detector control unit controlling a rotary drive of the X-ray detector using the X-ray detector rotation driving unit based on a detection result in the first detection unit;
a target rotation amount calculation unit that calculates a target rotation amount required to change an orientation of the X-ray detector that moves with the main body to an original orientation of the main body before the movement based on a first rotation amount detected by the first detection unit;
an X-ray detector rotation control unit that commands the X-ray detector rotation driving unit to rotate the X-ray detector based on the target rotation amount calculated by the target rotation amount calculation unit;
a rotatably supporting unit supporting the holding unit for the main body; and
a second detection unit detecting a second rotation amount of the supporting unit:
wherein the target rotation amount calculation unit calculates the target rotation amount based on the first rotation amount detected by the first detection unit and the second rotation amount detected by the second detection unit.

2. The mobile X-ray diagnostic apparatus according to claim 1, further comprising:
a command entry unit entering commands for start and end of detection by the first detection unit and the second detection unit,
wherein the first detection unit and the second detection, based on positions of the main body and the supporting unit, detect a displacement from a first time point where a detection start command was entered by the command entry unit to a second time point where a detection end command is entered as a rotation amount.

3. The mobile X-ray diagnostic apparatus according to claim 2, further comprising:
a third detection unit detecting a third rotation amount of the X-ray detector,
wherein the target rotation amount calculation unit calculates the target rotation amount in further addition to the third rotation amount of the X-ray detector detected by the third detection unit while the first detection unit and the second detection unit start and end the detection, and
wherein the third detection unit detects the third rotation amount of the X-ray detector rotated by a command for rotation by the target rotation amount from the X-ray detector rotation control unit to the X-ray detector rotation driving unit, the X-ray detector rotation control unit determines whether a rotation equivalent to the target rotation amount has ended or not based on an angle deviation between a relevant rotation amount and the target rotation amount.

4. The mobile X-ray diagnostic apparatus according to claim 1, further comprising:
wheels movable on the floor surface,
wherein the first detection unit is comprised of a sensor that detects a rotation amount of the wheels.

5. The mobile X-ray diagnostic apparatus according to claim 1, wherein the first detection unit is comprised of a sensor that detects angular acceleration of the main body.

6. The mobile X-ray diagnostic apparatus according to claim 1, wherein the second detection unit is comprised of a sensor that detects a rotation amount of the supporting unit or a sensor that detects angular acceleration of the supporting unit.

7. The mobile X-ray diagnostic apparatus according to claim 3, wherein the third detection unit is comprised of a sensor that detects a rotation amount of the X-ray detector rotation driving unit or a sensor that detects angular acceleration of the X-ray detector.

8. The mobile X-ray diagnostic apparatus according to claim 2, further comprising:
   a radiation button entering a fluoroscopy command to detect a dynamic picture image by irradiating the X-ray from the X-ray source,
   wherein the command entry unit comprises the radiation button, and starts the detection when a fluoroscopy start command is entered from the radiation button, and
   wherein the first detection unit and the second detection unit continue the detection until a fluoroscopy end command is entered from the radiation button.

* * * * *